United States Patent [19]

Lederman et al.

[11] 4,127,034
[45] Nov. 28, 1978

[54] DIGITAL RECTILINEAR ULTRASONIC IMAGING SYSTEM

[75] Inventors: Frank L. Lederman; Jerome J. Tiemann, both of Schenectady, N.Y.

[73] Assignee: General Electric Company, Schenectady, N.Y.

[21] Appl. No.: 863,882

[22] Filed: Dec. 23, 1977

[51] Int. Cl.$^2$ .......................................... G01N 29/00
[52] U.S. Cl. .................................................... 73/626
[58] Field of Search ................. 73/607, 619, 620, 624, 73/625, 626

[56] References Cited

U.S. PATENT DOCUMENTS

| | | | |
|---|---|---|---|
| 3,481,186 | 12/1969 | Cellitti et al. ....................... | 73/626 X |
| 3,789,833 | 2/1974 | Bom .................................... | 73/626 X |
| 3,911,730 | 10/1975 | Niklas ................................... | 73/624 |
| 4,012,952 | 3/1977 | Dory ................................... | 73/626 X |
| 4,058,003 | 11/1977 | Macovski .......................... | 73/620 X |
| 4,070,642 | 1/1978 | Iinuma et al. ...................... | 73/626 X |

*Primary Examiner*—Charles A. Ruehl
*Attorney, Agent, or Firm*—Donald R. Campbell; Joseph T. Cohen; Marvin Snyder

[57] ABSTRACT

A B-scan ultrasonic imager produces a rectilinear image and has a linear transducer array with only one switch per element. Individual elements or overlapping transmit subarrays are selected sequentially to generate pulses of ultra-sound. Received echo signals are sequentially sent down a long shift register delay line, are tapped off at the pulse repetition rate, and delayed by different amounts in the several channels and summed to effect time delay focusing of the echoes. The video output signal is post-processed to improve the TV monitor picture; interpolated image lines are conveniently derived with this architecture.

24 Claims, 5 Drawing Figures

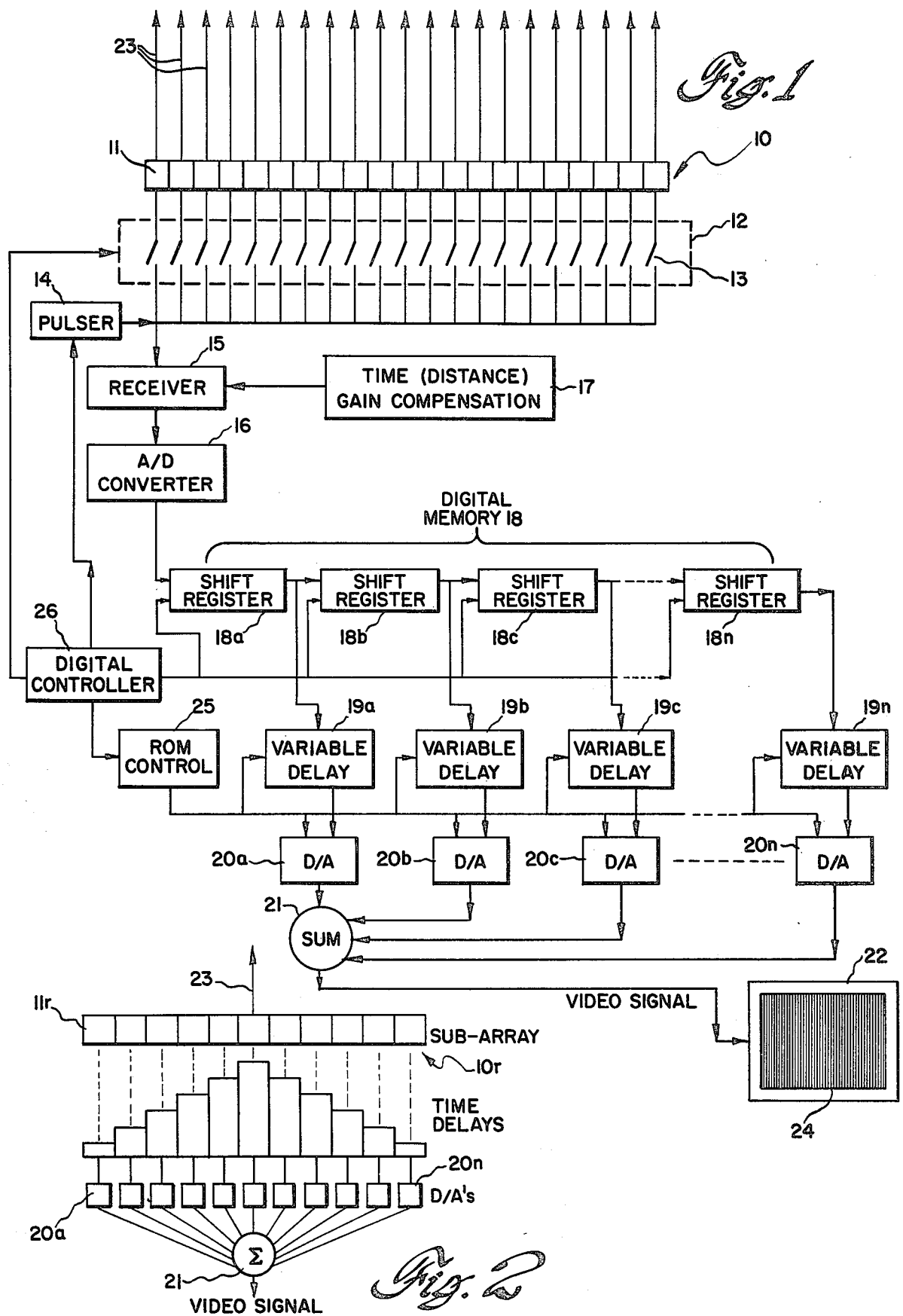

DIGITAL RECTILINEAR ULTRASONIC IMAGING SYSTEM

BACKGROUND OF THE INVENTION

This invention relates to a method and system for ultrasonic imaging, and more particularly to a method of ultrasonic imaging and a digital rectilinear real time ultrasonic imaging system capable of scanning rectilinearly which uses time delay focusing and does not require an impractically large number of multiplex switches.

The two most successful types of real time ultrasound systems, imaging at 30 frames per second or faster, are the Fresnel focused systems and the steered beam, phased array systems. The Fresnel approach is disclosed in U.S. Pat. No. 3,911,730 and in French Publication No. 2,292,978 by Pierre Alais, inventor, entitled "Improvements in Methods and Devices for Ultrasonic Imaging," and as described by the latter uses multiplex switches and shift registers to produce rectilinear images. There are several inherent limitations, such as relatively poor depth resolution, and these systems may not be capable of producing good images of the heart or good grey scale images. The phased array applied as a cardiac scanner is explained in "A New Ultrasound Imaging Technique Employing Two-Dimensional Electronic Beam Steering" by Thurstone and Von Ramm, *Acoustical Holography*, Vol. 5, 1974, Plenum Press, New York, pp. 249-259. The phased array utilizes time delay focusing and therefore has better resolution than in Fresnel focusing, but produces a sector scan image that is less pleasing and harder to manipulate.

It would be desirable to have a real time electronic scanner that will produce a rectilinear image and which uses time delay focusing for higher resolution. In the past there have been suggestions to achieve this goal, however, all of the suggested implementations require very large numbers of multiplex switches. For example, if each of 160 transducers is delayed by 32 different time delays, more than 5000 switches would be required. This is not feasible. The present invention has all of the advantages of Fresnel and phased array systems but is implemented with a reasonable number of multiplex switches.

SUMMARY OF THE INVENTION

An exemplary embodiment of the digital rectilinear ultrasonic imaging system has a relatively long linear transducer array with equally spaced transducer elements, and employs a multiplex switch array with only one switch per element. The multiplex switches select one element at a time in sequence to thereby generate a series of transmitted acoustic pulses, and the received echo signal output of a selected transducer is converted to digital echo amplitude data and fed to a segmented digital memory such as a shift register delay line. Each shift register or other memory unit is capable of storing the echo data derived from one receive element, and after a number of transmitted pulses equal to the number of elements in a receive sub-array the memory is filled up and entry of new data results in loss of earlier acquired data. Parallel signal processing channels are connected to the outputs of every shift register and each is comprised of a delay device and D/A converter, or vice versa. Stored data read out of the shift registers into the following shift register is also tapped off into the parallel processing channels, where the data is delayed by different amounts corresponding to the delay time differences of a focused array. The delayed analog signals are summed to generate a video output signal for controlling the electron beam intensity of a cathode ray tube, which displays a rectilinear image without the need for a scan converter.

The signal-to-noise ratio is improved by exciting individual transducers with a series of coded pulses and including a matched filter in the receiving channel. Alternatively, a transmit subarray of several elements can be pulsed in a symmetrical time sequence to generate a pulse of ultrasound with a synthesized rounded acoustic wavefront. The use of a rounded wavefront avoids the relatively narrow beam profile produced when the elements are fired simultaneously. Thus a broader beam is produced. A central transducer of sequentially selected and overlapping transmit sub-arrays serves as a receive element and is coupled to the receiving channel by a multiplexer. The segmented digital memory can be implemented with properly addressed random access memories and it is not essential, as more broadly defined, that the data be transfered from one memory unit to the next so long as the position in the receive sub-array is established.

Post-processing of the video output signal to improve picture quality is facilitated by the digital rectilinear architecture because the spatial relationship of adjacent beams is uniform. An image line is generated centered on every transducer, with the possible exception of those near either end, and one or more interpolated image lines between adjacent actually generated lines are conveniently obtained. A grey level slicer with provision for clipping the voltage level at both ends of the video signal and an adaptive brightness-contrast control are also discussed.

BRIEF DESCRIPTION OF THE DRAWINGS

FIG. 1 is a simplified system block diagram of the digital rectilinear real time ultrasonic imager;

FIG. 2 is a diagram illustrating time delay focusing of echo data from a sub-array of receive transducer elements;

DESCRIPTION OF THE PREFERRED EMBODIMENT

Figure 3:
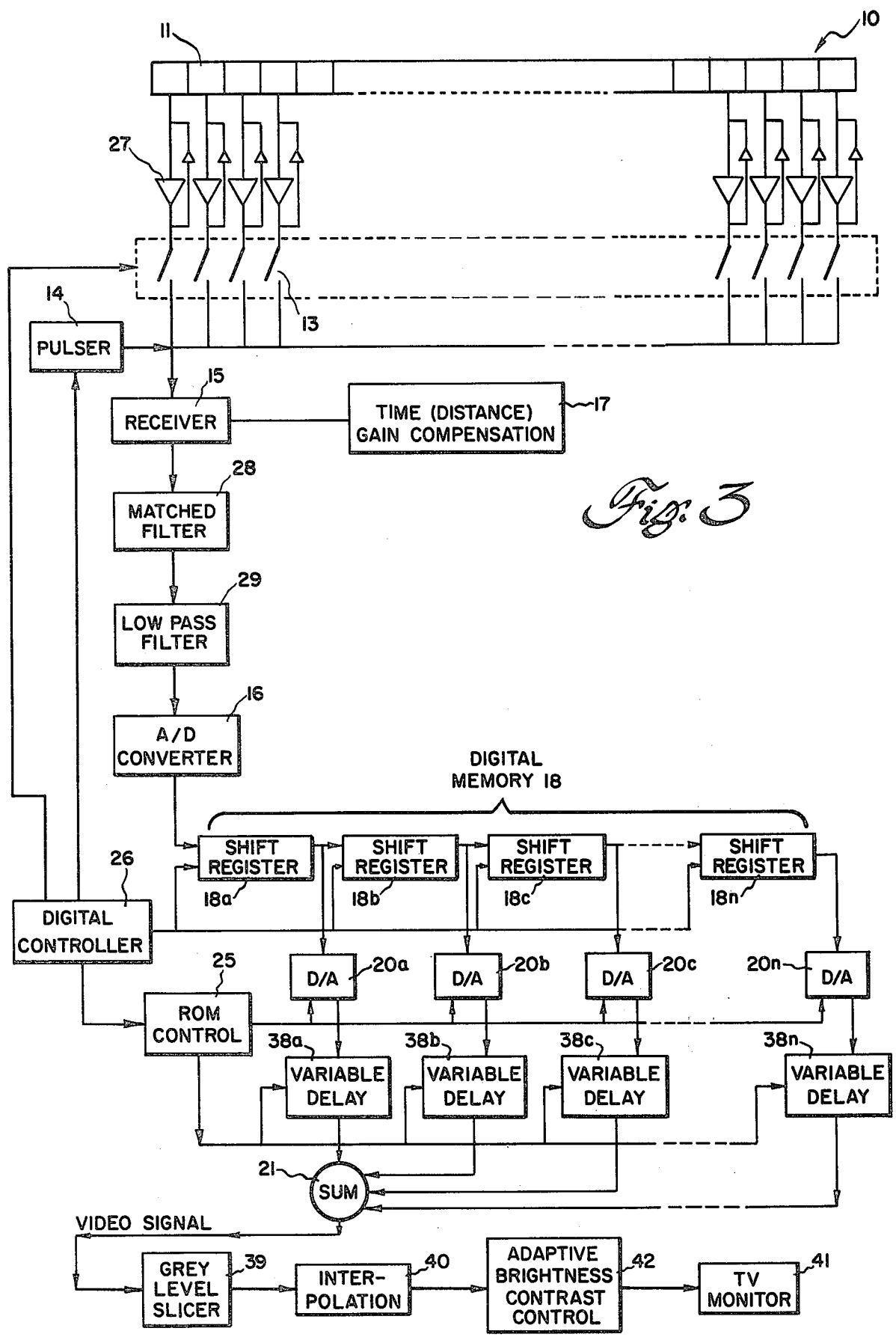
FIG. 3 is a modification of FIG. 1 with the addition of features in the receiving channel for improved signal-to-noise ratio and in the video signal processing channel to improve image quality.

The architecture of the digital rectilinear real time ultrasonic imaging system is illustrated in simplified block diagram form in FIG. 1 without those features, which will be discussed later, to improve the signal-to-noise ratio of the received echo signal and to improve the quality of the video image. In this implementation, the transducer elements of a linear transducer array are selected one at a time by an array of multiplex switches, but only one switch per transducer is required. The output of the selected transducer is digitized and the digital words representing sequential samples are sent down a long, segmented digital delay line memory. At times corresponding to one transmit pulse repetition period, the digital outputs are tapped off and fed to digitally controlled delay lines whose length correspond to the delay time differences of a focused array. The delayed echo data from the delay elements is converted to analog form and summed to provide a focused output. This is the video signal which is fed to a television monitor to control the electron beam intensity. What this architecture accomplishes is to trade off a large number of multiplex switches against an equal number of stored samples, avoiding the problem of an impractically large number of switches and connections while taking advantage of the fact that memory is relatively cheap and that a small number of pins on an integrated circuit memory device can serve a large number of memory cells.

In FIG. 1, linear transducer array 10 has a large number of equally spaced electroacoustical transducer elements 11 made of piezoelectric material. Typically there are 100 to 200 elementary transducers in the array spaced every millimeter. A multiplex switch array 12 is comprised by only one switch 13 per transducer element, which are closed one at a time starting from one end to select transducers 11 in sequence for each transmitted and received pulse. Switches 13 are electronically controlled solid state switches of a type which do not degrade the signal-to-noise ratio, and each switch is connected directly to the individual transducer or through a preamplifier to increase the echo signal level. A pulser 14 generates a series of excitation pulses in coordination with the successive closing of switches 13 to energize transducer elements 11 in sequence. Each transducer approximates a point source and produces a transmitted pulse of ultrasound with a convex or spherical wavefront which illuminates a large aperture in the insonified object region. Acoustic energy reflected by targets in the illuminated region are detected by the same transducer elements, and the received echo electrical signal or echo trace is fed to a receiving channel.

A single receiving channel including at least a receiver 15 and an analog-to-digital converter 16 is time-shared among all the transducer elements. The receiver gain is varied as a function of time according to a given curve to compensate for the attenuation of acoustic energy with increasing distance into the object, and time gain compensation circuit 17 can take various forms as is known in the art. A/D converter 16 samples the input analog signal at a high rate and generates a large number of digital echo amplitude data to be fed to memory. It is theoretically possible to perfectly recover an analog signal from a sequence of discrete samples provided the sampling rate is at least twice as high as the highest frequency present in the input data. For practical reasons, however, a number like 2.5 times the maximum frequency is preferred. Assuming that the highest ultrasonic frequency is approximately 2.0 megahertz, a sampling rate of 5 megahertz will be sufficient. The digital echo data preferably has a resolution of 8 bits or 8 bits + sign.

The memory is a segmented digital memory comprised of a plurality of memory units each sufficiently large to store the digitized echo data from a single receive transducer element, and can be a segmented delay line. Digital memory 18 is a long, segmented digital delay line comprised of a plurality of serially connected shift register memory units 18a–18n. The total number of shift registers is equal to the number of transducer elements in a receive sub-array, such as 32 where the total number of elements in linear transducer array 10 is 100, or 64 where the total number is 200 elements. Digital echo data generated by the first element in array 10 and fed out of A/D converter 16 is clocked into the first shift register 18a. The total number of sampling points corresponding to the lengths of the individual shift registers can be between 1024 and 2048 bits. At the same time that digital echo data from the second transducer element is clocked into shift register 18a, stored echo data is read out of shift register 18a into shift register 18b. The process repeats as the elements in array 10 are pulsed on at a time, always entering the new data into the first shift register and sending the already stored data down the delay line to the next shift register in sequence. Thus, after N transmitted and received pulses, the first N tranducers in the array have been selected, and their outputs are simultaneously present at the N steps of the long segmented delay line.

After selection of the next transducer element and upon clocking echo data into shift register 18a, stored data read out for entry into shift register 18b is also fed to a receive element signal processing channel comprised of variable delay device 19a and a digital-to-analog converter 20a. There are a plurality of such parallel signal processing channels comprised of variable delay devices 19a–19n and D/A converters 20a–20n, each channel being connected to the output tap of the shift register being read out. The amount of delay from channel to channel depends upon the position of the receive element in the receive sub-array and is chosen to focus the echoes. This is further explained in the discussion of FIG. 2. The delayed analog signals for the entire sub-array are now fed to a summing amplifier 21 to effect coherent summation. The focused output of summing amplifier 21 is the video signal to be fed to a cathode ray tube 22 as the Z control or to control the electron beam intensity. The image scan line which is synthesized by the time delay focusing technique is perpendicular to the longitudinal axis of the linear array, and thus no scan converter is required as was the case for the sector scan imagers.

In FIG. 2 is shown an illustrative receive sub-array 10R of twelve elementary receive transducers 11R, and the video signal generated by coherent summation of the delayed element echo signals represents image information along an acoustic scan line 23 that is normal to the sub-array at its midpoint. Assuming that the focal point is at a given range, an echo reflected by a target at the focal point is sensed by the elements at different times, depending on the position of the element in the sub-array, because of the differences in the length of the acoustic propagation paths. The magnitudes of the time delays of the individual received echo signals, indicated by rectangles of different lengths, compensate for acoustic path propagation delay differences. These are precomputed so as to correspond to the geometry of the receive beam in relation to the elements of the array. Within limits, these delays can be chosen to correspond to a central beam, a displaced beam, or a slightly angled beam. After conversion to analog data, the delayed echo signals are summed to produce the focused output. Delay devices 19a–19n in FIG. 1 can have a fixed delay if the focal point remains at a fixed range, but variable delay devices are needed for dynamic focusing in which the focal point is progressively at different distances from the linear array to attain improved image quality. In this case, the time delays are varied incrementally as the shift registers are read out into the receive element signal processing channels.

As successive transducers are selected one at a time for a transmitted and received ultrasound pulse, the digital echo amplitude data for each receive element enters the segmented delay line at shift register 18a, is transferred from one shift register to the next at the pulse repetition rate, and exits at shift register 18n. The data read out of the final shift register is lost. Thus, for a receive array of 32 elements, echo data for receive elements 1–32 is initially in the shift register memory, then echo data for elements 2–33, elements 3–34, and so on. At times corresponding to one pulse repetition, the digital echo data are tapped off and fed to delay devices 19a–19n and D/A converters 20a–20n, and the delayed signals from all the channels of the receive sub-array are summed to focus the echoes and generate a video signal. The digital rectilinear ultrasonic imager has a rectilinear scanning pattern with the spacing of acoustic scan lines 23 being equal to the transducer-to-transducer spacing, the scan beginning at one end of linear array 10 and proceeding to the other end. An image 24 is built up on the screen of cathode ray tube 22 scan line by scan line to form an image frame, and for a real time display the entire rectilinear scan and image formation is repeated at a rate of thirty frames per second or higher. TV monitor 22 is turned through 90° so that the electron beam scans along vertical scan lines rather than the usual horizontal lines.

The preferred method of operation at the beginning and end of the rectilinear scan, when fewer than an entire receive sub-array of elements have been excited or when a variable number of shift registers 18a–18n are empty, is that data is displayed as long as there is stored information in digital memory 18. At the beginning of a scan as the shift register memory units fill up, echo data is read out of any shift register containing information into the receive element signal processing channels for delaying the data and converting to analog form, and a variable number of delayed echo signals are summed by summing amplifier 21. At the end of the rectilinear scan after the last transducer element 11 in linear array 10 has been pulsed, the shift register memory units begin to empty out as data is transferred from one shift register memory unit to the next, and whatever data is present is processed at the same pulsed repetition rate through the delay and conversion channels for coherent summation and generation of a video output signal. Image lines at either side of the image are less reliable than those in central regions, but contain meaningful information.

The components of the digital rectilinear real time ultrasonic imaging system can be conventional, commercially available circuitry or can be readily developed based on the known prior art. Variable delay devices 19a–19n suitably are digital delay lines implemented in TTL (transistor-transistor-logic) shift registers together with TTL multiplexers to select the output tap having the correct time delay. The multiplexers are driven by a standard ROM (read only memory) control 25 to select the focal characteristics, such as Type 1702A electrically programmable read only memory manufactured by Intel Corp. System digital controller 26 controls the sequence of operation of multiplex switch matrix 12 and pulser 14, supplies clock pulses to shift registers 18a–18n in the digital memory, and determines the read out of stored data in ROM control 25 for the variable delay lines and the D/A converters. Digital controller 26 can be a hard-wired logic circuit but is preferably a properly programmed microcomputer or minicomputer. The memory units in digital memory 18 may also be conventional random access memories which are written into and read out of on every pulse of ultrasound. Moreover, a random access memory can be a variable delay device and with appropriate address circuitry can simulate the behavior of a variable length shift register.

The imaging system in FIG. 3 is essentially a modification of FIG. 1 with the addition of features in the receiving channel to improve the signal-to-noise ratio and in the video signal processing channel to improve the quality of the image. A preamplifier 27 is included between every elementary transducer 11 and multiplex switch 13 to increase the voltage level of the received echo electrical signal. Diodes associated with each preamplifier protects it from the high voltage excitation pulse. Instead of applying a single excitation pulse to the transducer element, a series of coded pulses such as a Barker Code can be used on transmission. An inverse code matched filter 28 is then placed in the receiving channel following receiver 15 to recover the sharp system impulse response required in this approach. A signal-to-noise improvement is achieved equal to the number of pulses in the code, which would be 13 in the Barker Code example, or as high as 100 if a radar code were used. Matched filter 28 can be a known type of CCD (charge coupled device) transversal filter. A low pass filter 29 is illustrated as a separate component in advance of the A/D converter because it is theoretically necessary to smooth the raw signal prior to sampling it. Actually, this function is provided by the transducer response, the cut off frequencies of the amplifier stages of the receiver, or the matched filter (if used).

Figure 4:
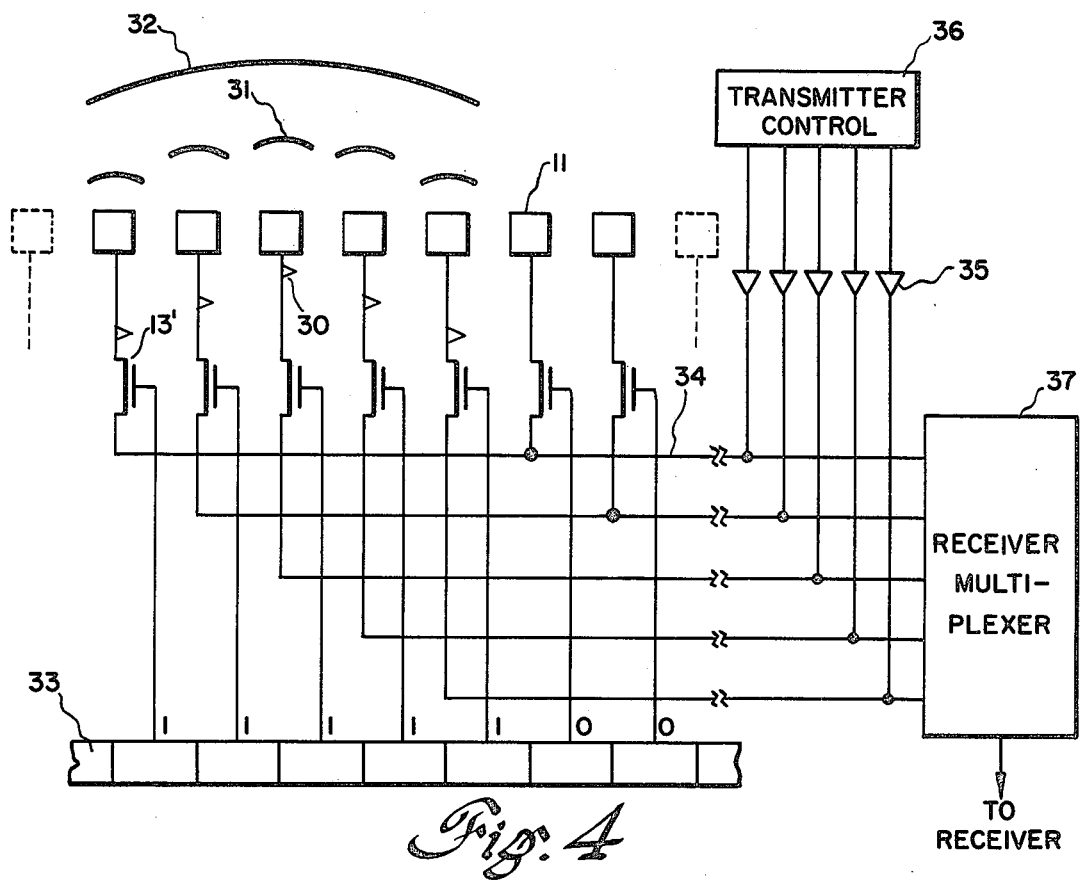
FIG. 4 is a schematic diagram of alternative and preferred transmit channel circuitry in which a sub-array of transducers are pulsed in sequence to generate a rounded wavefront.

In order to generate a transmitted pulse of ultrasound having a greater amount of acoustic energy, the preferred transmit channel circuitry in FIG. 4 has a sub-array of transducers which are pulsed in time sequence to generate a rounded acoustic waveform. The alternative is to energize a single transducer element with a high voltage excitation pulse. The new concept generates a larger energy pulse with a broad beam angle. An individual transmitter element illuminates a large aperture and the acceptance angle broadens as the transducer becomes more narrow. If four or five elements are pulsed at the same time, the acceptance angle decreases and the propagating energy has a straight of flat wavefront. The digital rectilinear system, however, requires a large acceptance angle so that transducers toward the end of a receive sub-array illuminate a target at the center of the sub-array and generates an echo signal which makes a contribution to the coherent summation. The exemplary transmit sub-array in FIG. 4 is comprised of five contiguous elements 11, but only the center element is the receive element. To simulate a virtual single element with a rounded acoustic wavefront that looks like the wavefront of one element if pulsed from behind the sub-array, an excitation pulse 30 is applied first to the center element, then the two adjacent elements on either side are pulsed and finally the two endmost elements. The convex wavefront for a single element is indicated at 31 and the synthesized rounded acoustic wavefront of the transmit sub-array is indicated at 32.

The transmit sub-array indexes along linear array 10 one transducer element per transmitted and received ultrasound pulse. An MOS (metal oxide semiconductor) transistor switch 13' is connected to each transducer element 11, and the gates of MOS switches 13' are individually controlled by one stage of a long shift register 33. A sub-array select word of five "1"'s is clocked down the shift register at the ultrasound repetition rate, applying voltages to the gates of the five selected MOS switches 13'. To energize the five selected elements as they transmit sub-array indexes down linear array 10 one element at a time while in every case selecting the center transducer as the receive element, there are five busses 34 respectively connected to separate pulsers 35 which are controlled by a transmitter control 36. All the busses are input to a receiver multiplexer 37 having a single output for supplying the echo signal to receiver 15. The first and sixth elements are coupled through their MOS switches to the first bus 34, the second and seventh elements to another bus, the third and eighth elements to still another bus, and so on. An excitation pulse generated by the third pulser 35 is applied only to the center transducer of the selected sub-array, the switches to other transducers coupled to that same bus being closed. Then the second and fourth busses are pulsed and finally only the first and fifth busses are pulsed. Receiver multiplexer 37 selects the third bus 34 to be connected to the output because the center transducer of the sub-array is always the receive element. The number of elements in a transmit sub-array is chosen to result in a desired signal-to-noise improvement. As compared to pulsing a single element, it is repeated, this concept produces an ultrasound pulse having a larger amount of acoustic energy with a broad acceptance angle.

Referring to FIG. 3, a modification of the receive element echo signal processing channels is that data read out of shift register memory units 18a–18n passes first through digital-to-analog converters 20a–20n and then through variable delay devices 38a–38n. As compared to FIG. 1 the processing sequence is reversed, and in this case the analog delay devices can be the same as those in sector scan ultrasonic imagers. The coherent summation process is the same in both cases.

Figure 5:
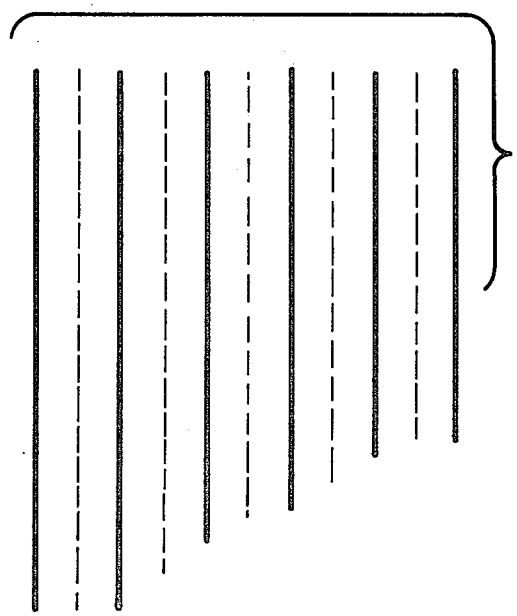
FIG. 5 is a sketch of interlaced cathode ray tube scanning lines produced by the interpolator in FIG. 3.

The parallel image line geometry of the digital rectilinear real time scanner facilitates post-processing of the video signal generated by summing amplifier 21 to display a higher quality image which is pleasing to the eye. A grey level slicer component 39 performs the function of clipping the voltage level at both the bright and dark ends of the video signal, so as to spread the interesting region over the entire available dynamic range of a cathode ray tube. Conventional diode clipping circuits can be used. A relatively simple interpolation system 40 is made possible by the fact that the geometry of the data points does not change with range. Image lines in the display actually generated by the video signal from summing amplifier 21 are shown in black in FIG. 5, and there is one image line per transducer element in linear array 10. Scanning lines on the screen of the monitor 41 between the image lines in the absence of interpolation would be shown as black. The function of interpolation circuit 40 is to generate one or more intermediate image lines, shown dashed in the figure, whose brightness is derived from the brightness levels of the foregoing and succeeding actually generated image lines. In the case where one interpolated line is to be generated, its brightness at every point should be the average of the brightness levels of the adjacent actually generated lines. Greater numbers of interpolated lines can be generated by weighting and combining the contributions from the foregoing and succeeding actually generated image lines. This variable weight interpolation eliminates the staircase effects associated with constant fill-in, due to the many lines which smoothly vary from one situation to the next. Implementation of the interpolation system is with a memory for the proceeding video signal and addition circuits.

Adaptive brightness-contrast control 42 can be such as is described in "Adaptive Gain Control For Dynamic Ultrasound Imaging" by A. Declercq and N. G. Maginess, 1975 *IEEE Ultrasonics Symposium Proceedings*, pp. 59–63. To explain the problem solved by this control, time gain compensation can be used to compress the dynamic range of ultrasonic B-Scan signals to a more practical range, but the resulting signal may not always match the dynamic range of the display. If a small dense object were present, for instance, the echo from it could be very large and could saturate the display even though it had very little effect on the overall average of the signal. The referenced adaptive control examines peak signals in several range segments, anticipating required gains from a progressively updated store. Isolated strong echoes are ignored to avoid loss of lower level details.

The digital rectilinear system is a B-Scan ultrasonic imager capable of displaying a tomographic slice of the insonified region in real time on the screen of a conventional TV monitor. There are many medical diagnostic examination applications and also industrial inspection applications. The system is similar to the Fresnel systems of P. Alais in the sense that a sub-array of transducers is utilized to focus along an axial line, and this line is successively positioned over adjacent elements by propagating a logic control signal to an array of multiplex switches associated with each transducer element. It is also similar to phased array time delay systems in the sense that a single cycle pulse is employed rather than a pulse train, and focus is achieved by time delay rather than by phase addition. Thus, this new architecture combines the best features of both approaches. Namely, it produces an easily displayed rectilinear output format rather than a sector scan format, together with the high resolution of a time delay system. The digital rectilinear scanner can be reduced to practice with integrated circuit and discrete components presently available. Interpolated lines in the display centered between transducers can be computed just as easily as along lines centered on transducers.

While the invention has been particularly shown and described with reference to several preferred embodiments thereof, it will be evident to those skilled in the art that various changes in form and details may be made therein without departing from the spirit and scope of the invention.

What is claimed is:

1. A digital rectilinear ultrasonic imaging system comprising
   a linear transducer array having a plurality of electroacoustic transducer elements.
   a multiplex switch array comprising one switch per transducer element for connecting said transducers in sequence to pulser means and to a receiving channel for sampling received echo electrical signals and generating echo amplitude data,
   a segmented digital memory including a plurality of memory units each capable of storing the echo data derived from one transducer,
   means for successively delaying echo data read out in parallel from said memory units and for generating delayed analog signals, to thereby focus the received echoes derived from plural contiguous transducers, and means for successively summing the delayed analog signals to produce a video output signal.

2. The imaging system of claim 1 wherein the number of memory units in said segmented digital memory is equal to the number of contiguous elements in a receive sub-array.

3. The imaging system of claim 2 wherein said means for delaying echo data read out of memory and for generating delayed analog signals comprises a plurality of parallel processing channels connected to the outputs of said memory units, each processing channel being comprised of a delay device and a digital-to-analog converter, said memory units further being serially coupled so that stored data read out into a processing channel is also read into the following memory unit.

4. The imaging system of claim 2 wherein said means for delaying echo data read out of memory and for generating delayed analog signals comprises a plurality of parallel processing channels connected to the outputs of said memory units, each processing channel being comprised of a digital-to-analog converter and a delay device, said memory units further being serially coupled so that stored data read out into a processing channel is also read into the following memory unit.

5. The imaging system of claim 1 wherein said pulser means is a single pulser and said multiplex switch array is operative to connect said transducers one at a time in sequence to said pulser and to said receiving channel.

6. The imaging system of claim 5 wherein said pulser generates a series of coded pulses for exciting each transducer element, and wherein said receiving channel further includes a matched filter to improve the signal-to-noise ratio.

7. The imaging system of claim 1 wherein said linear transducer array is divisible into multiple transmit sub-arrays of contiguous elements and a central element in every transmit sub-array is designated a receive element, said pulser means is comprised of a plurality of pulsers, and said receiving channel further includes receiver multiplexer means, said multiplex switch array being operative to connect said transmit sub-arrays in sequence to said pulsers to excite the elements thereof in time sequence and generate a pulse of ultrasound with a rounded acoustic wavefront.

8. A digital rectilinear ultrasonic imaging system comprising a linear transducer array having a plurality of electro-acoustic transducer elements which are individually operable to generate a pulse of ultrasound and a received echo electrical signal, a multiplex switch array comprising one switch per transducer element for connecting said transducers, one at a time in sequence, to a pulser and to a receiving channel wherein the received echo signals are sampled and converted to digital echo amplitude data, a segmented digital memory including a plurality of serially connected memory units each capable of storing the echo data derived from one element, parallel signal processing channels for echo data read out of said memory units substantially in parallel that are effective to delay the echo data and to convert the data to delayed analog signals, to thereby focus the received echoes derived from plural contiguous elements, and means for summing the delayed analog signals to produce a video signal and for post-processing and displaying successively generated video signals as a visual image of the insonified object region.

9. The imaging system of claim 8 wherein said memory units are shift registers serially connected together to form a segmented delay line, said parallel signal processing channels being connected to the outputs of said shift registers and each including a delay device and a digital-to-analog converter, whereby stored data read out of a shift register into a signal processing channel is also read into the following shift register, and wherein the number of shift registers is equal to the number of elements in a receive sub-array.

10. The imaging system of claim 8 wherein said memory units are shift registers serially connected together to form a segmented delay line, said parallel signal processing channels being connected to the outputs of said shift registers and each including a digital-to-analog converter and a delay device, whereby stored data read out of a shift register into a signal processing channel is also read into the following shift register, and wherein the number of shift registers is equal to the number of elements in a receive sub-array.

11. The imaging system of claim 8 wherein said means for post-processing successively generated video signals includes means for clipping the voltage level at either end of said video signal, means for interpolating additional image lines between actually generated image lines, and adaptive brightness-contrast control means.

12. The imaging system of claim 8 wherein said pulser generates a series of coded pulses for exciting each transducer element, and wherein said receiving channel further includes a matched filter to improve the signal-to-noise ratio.

13. A digital rectilinear ultrasonic imaging system comprising a linear transducer array having a plurality of electro-acoustic transducer elements divisible into multiple transmit sub-arrays of elements each operable to generate a pulse of ultrasound, one element in every transmit sub-array being a receive element operable to generate a received echo electrical signal, a multiplex switch array comprising one switch per transducer element for sequentially connecting said transmit sub-arrays to pulser means and for sequentially connecting said receive elements through a receiver multiplexer to a receiving channel wherein the echo signals are sampled and converted to digital echo amplitude data, a segmented digital memory including a plurality of serially connected memory units each capable of storing the echo data derived from one receive element, parallel signal processing channels for echo data read out of said memory units substantially in parallel that are effective to delay the echo data and to convert the data to delayed analog signals, to thereby focus the received echoes derived from plural contiguous receive elements, and means for summing the delayed analog signals to produce a video signal and for processing and displaying successively generated video signals as a visual image of the insonified region.

14. The imaging system of claim 13 wherein said memory units are shift registers serially connected together to form a segmented delay line, said parallel signal processing channels being connected to the outputs of said shift registers and each including a delay device and a digital-to-analog converter, whereby stored data read out of a shift register into a signal processing channel is also read into the following shift register, and wherein the number of shift registers is equal to the number of elements in a receive sub-array.

15. The imaging system of claim 13 wherein said memory units are shift registers serially connected together to form a segmented delay line, said parallel signal processing channels being connected to the outputs of said shift registers and each including a digital-to-analog converter and a delay device, whereby stored data read out of a shift register into a signal processing channel is also read into the following shift register, and wherein the number of shift registers is equal to the number of elements in a receive sub-array.

16. The imaging system of claim 13 wherein said means for post-processing successively generated video signals includes means for clipping the voltage level at either end of said video signal, means for interpolating additional image lines between actually generated image lines, and adaptive brightness-contrast control means.

17. The imaging system of claim 13 wherein said pulser means is comprised of a plurality of pulsers and control means therefor for generating excitation pulses in time sequence for the elements of a selected transmit sub-array such that a central element is pulsed first and successively outer pairs of elements are pulsed sequentially to generate a pulse of ultrasound with a rounded acoustic wavefront.

18. A method of ultrasonic imaging comprising the steps of
sequentially pulsing selected transducer elements of a linear transducer array to generate a series of transmitted acoustic pulses while alternatively generating received echo electrical signals,
successively amplifying said echo signals and converting to digital echo amplitude data,
storing the echo data in a plurality of digital memory units,
periodically reading out the stored echo data from said memory units into parallel processing channels wherein the echo data is delayed and converted to delayed analog signals to thereby focus the received echoes derived from plural contiguous elements, and
summing the delayed analog signals to produce a video output signal.

19. The method of claim 18 wherein the step of sequentially pulsing selected transducer elements of a linear transducer array comprises pulsing said elements one at a time in sequence, and wherein the step of periodically reading out the stored echo data from said memory units comprises reading out the stored data into the following memory units and into the parallel processing channels at the transmitted pulse repetition rate.

20. The method of claim 18 wherein the step of sequentially pulsing selected transducer elements of a linear transducer array comprises pulsing transmit sub-arrays of elements in sequence to generate a series of transmitted acoustic pulses with a rounded wavefront, one element of each transmit sub-array being selected as a receive element, and wherein the step of periodically reading out the stored echo data from said memory units comprises reading out the stored data into the following memory units and into the parallel processing channels at the transmitted pulse repetition rate.

21. The method of claim 18 further including the steps of post-processing the video output signal to improve the quality of the image and feeding the signal to a cathode ray tube to display a rectilinear image, the post-processing including at least deriving interpolated image lines between adjacent actually generated image lines.

22. A method of ultrasonic imaging comprising the steps of
sequentially pulsing selected transducer elements of a linear transducer array to generate a series of transmitted ultrasound pulses while alternately generating received echo electrical signals.
successively amplifying said echo signals and converting to digital echo amplitude data,
storing the echo data in a segmented digital delay line along which the data advances serially,
tapping off echo data from the segments of said digital delay line at the ultrasound pulse repetition rate into parallel processing channels wherein the echo data is delayed to focus the received echoes and is converted to delayed anaolog signals,
summing the delayed analog signals to produce a video signal, and
feeding the video signal to a cathode ray tube to control the electron beam intensity and generate a rectilinear image.

23. The method of claim 22 wherein the step of storing the echo data in a segmented digital delay line comprises storing the data in a plurality of serially connected digital shift registers equal in number to the number of elements in a receive sub-array.

24. The method of claim 23 wherein the step of feeding the video signal to a cathode ray tube comprises post-processing the video signal to improve the quality of the rectilinear images by deriving interpolated image lines between adjacent actually generated image lines.

* * * * *